United States Patent [19]

Kronstadt

[11] Patent Number: 5,387,200
[45] Date of Patent: Feb. 7, 1995

[54] PORTABLE APPLICATOR FOR APPLYING SKIN PROTECTION FLUIDS

[75] Inventor: Samuel W. Kronstadt, Ellicott City, Md.

[73] Assignee: Sun-Safe Technologies Limited Partnership, Ellicott City, Md.

[21] Appl. No.: 179,208

[22] Filed: Jan. 10, 1994

[51] Int. Cl.6 ............................................. A61M 35/00
[52] U.S. Cl. ..................................... 604/290; 239/305
[58] Field of Search .................... 604/289, 290; 4/615; 239/303, 305; 222/132, 608, 400.7, 138

[56] References Cited

U.S. PATENT DOCUMENTS

| | | | |
|---|---|---|---|
| 557,878 | 4/1896 | Pownall | 239/305 |
| 2,943,797 | 7/1960 | Neilson | 239/305 |
| 3,380,658 | 4/1968 | Stasz | 239/305 |
| 3,383,044 | 5/1968 | Norstrud | 239/305 |
| 3,797,744 | 3/1974 | Smith | 239/305 |
| 3,870,233 | 3/1975 | Wilhelm et al. | 239/305 |
| 4,893,729 | 1/1990 | Iggulden | 222/144.5 |

Primary Examiner—Jerome L. Kruter
Attorney, Agent, or Firm—Oblon, Spivak, McClelland, Maier & Neustadt

[57] ABSTRACT

A process and apparatus is utilized to dispense a variety of skin protection fluids such as suntan lotions and oils on an individual's skin depending on the individual's particular needs or preference. The system applies the lotions and oils directly to the skin and enables an operator of the system to spray the lotions evenly on the individual and especially in hard-to-reach areas of the individual. The method and apparatus of the present invention utilizes an air compressor, pressure containers and spray devices to deliver the lotions and oils. Skin protection fluids having distinct skin protection factors are each stored in individual pressure containers and delivered from the pressure container through the use of an air compressor and an air pressure regulator. A nozzle and flexible hose arrangement is utilized to apply the skin protection fluid onto the individual.

11 Claims, 3 Drawing Sheets

PORTABLE APPLICATOR FOR APPLYING SKIN PROTECTION FLUIDS

BACKGROUND OF THE INVENTION

1. Field of the Invention

The present invention relates to a method and apparatus for selectively applying a variety of skin protection fluids such as suntan lotions and oils on an individual's skin. The type of skin protection fluid applied can be selected from a variety of skin protection fluids having different SPF factors (skin protection factor).

2. Description of the Related Art

When people are at public bathing areas such as beaches, rivers, pools, etc., proper skin protection lotions and oils are necessary to protect individuals from harmful rays such as ultraviolet rays from the sun.

When individuals are at a beach, the situation usually arises in which the individual may run out of suntan lotion or may not have a suntan lotion which has the specific SPF factor that the individual needs for protection. When suntan lotion is not readily available, such as on beaches where there is no convenient access to stores, obtaining a bottle of suntan lotion may be burdensome and time consuming. Also, even if a store is accessible to the beach, the possibility also exists that the store may not have the suntan lotion necessary for that specific individual.

Additionally, in situations where a large family or group of individuals are together on the beach, it is likely that each individual in the family or group may require skin protection fluids of different SPF factors. Accordingly, the family or group will have to carry a bag which would include several bottles of skin protection fluid. This may become cumbersome when travelling to a beach since other accessories such as beach chairs, towels, umbrellas and coolers also need to be carried.

Also, in applying skin protection fluid to an individual's skin, for maximum protection it is necessary to apply the skin protection fluid over the entire exposed surface area of the individual's skin. If the individual is alone, this is impossible since an individual cannot adequately apply skin protection fluid onto hard-to-reach areas of his or her own back. Accordingly, it is necessary to utilize the services of a second individual to apply the skin protection fluid on hard-to-reach areas such as the back and upper neck.

SUMMARY OF THE INVENTION

Accordingly, an object of the present invention is to provide for a novel method and apparatus for selectively applying a variety of skin protection fluids on an individual's skin. The application system of the present invention selectively dispenses a variety of skin protection lotions and oils depending on the individual's particular needs or preference. In view of the health risk involved with prolonged exposure to the sun, the system of the present invention will offer protection to individuals or groups where none may be available.

The system of the present invention applies skin protection lotions and oils directly to the skin and the operator of the system will be able to spray lotions evenly on the individual, especially in hard-to-reach areas such as the back and neck. This can also be desirable to individuals having for example, arthritis, since it is very difficult for individuals having arthritis to reach hard-to-reach areas of his or her body. The system can also be portable which therefore extends the range of the use of the system.

Accordingly, the present invention provides for a method for selectively applying a variety of skin protection fluids on an individual's skin. The method comprises the steps of storing a plurality of skin protection fluids having a different skin protection factor in a plurality of pressure containers such that each pressure container contains a distinct skin protection fluid, each of the pressure containers comprising an outlet for permitting a discharge of the skin protection fluid; connecting each of the pressure containers containing the skin protection fluid to an air compressor, the outlet of each of the pressure containers being operatively connected to an adjustable air pressure regulator for controlling a discharge air pressure from the air compressor and a control valve for controlling a flow of the skin protection fluid from the pressure container; fluidly connecting the control valve of each of the pressure containers to a single control nozzle having an adjustable orifice; selecting a skin protection fluid to be applied to the individual's skin from the plurality of skin protection fluids in each of the pressure containers; adjusting the air pressure regulator of the pressure container containing the selected skin protection fluid so as to provide a desired discharge air pressure based on at least a viscosity of the selected skin protection fluid for discharging the selected skin protection fluid; opening the control valve of the pressure container containing the selected skin protection fluid to permit a discharge of the selected skin protection fluid; and applying the selected skin protection fluid on the individual through the nozzle.

The present invention also relates to an apparatus for applying a variety of skin protection fluids on an individual's skin. The apparatus comprises a plurality of pressure containers, each one of the pressure containers comprising a skin protection fluid having a different skin protection factor and an outlet for discharging the skin protection fluids, each of the pressure containers being operatively connected to a control valve for controlling a flow of said skin protection fluid from said pressure container; a frame for holding each of the pressure containers containing the skin protection fluids; an air compressor mounted on the frame, the air compressor being operatively connected to each of the pressure containers to provide a discharge pressure for discharging a skin protection fluid from the pressure container through the outlet; a single nozzle for applying the skin protection fluid discharged from the pressure container to an individual's skin, the single nozzle having an adjustable orifice and being fluidly connected to each of the control valves of the pressure containers; and an adjustable pressure regulator operatively connected to each one of the pressure containers for adjusting the discharge pressure from the air compressor based on at least a viscosity of the skin protection fluid selected to be discharged and applied to the individual's skin, wherein a size of the orifice of the nozzle is adjusted based on the selected discharge pressure and the selected skin protection fluid.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
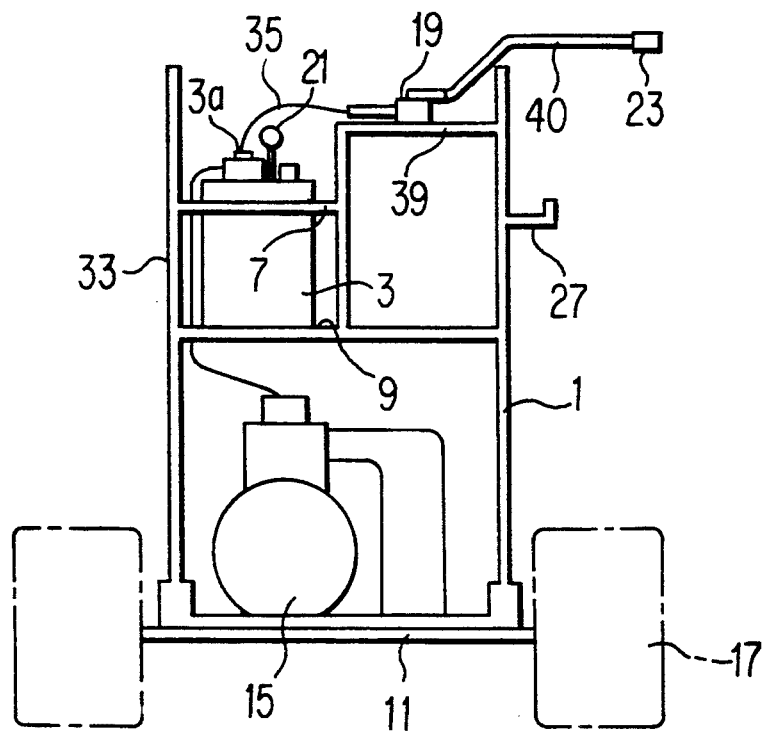
FIG. 1 is a side view of the frame of the present invention for holding the air compressor and the pressure containers containing the skin protection fluids.
Figure 3:
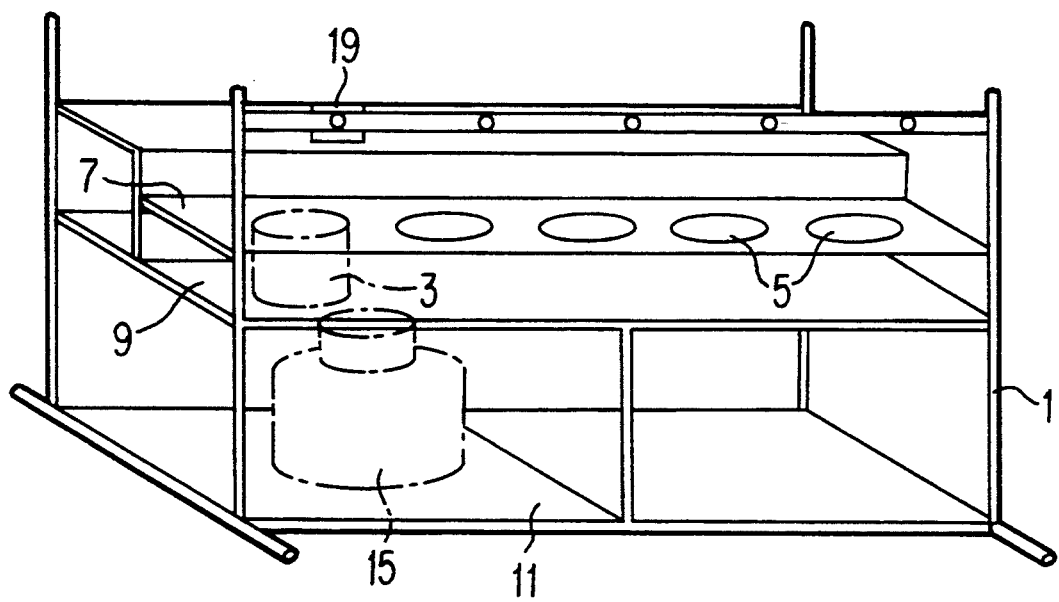
FIG. 3 is a perspective view of the frame for holding the air compressor and pressure containers containing the skin protection fluids.
Figure 5:
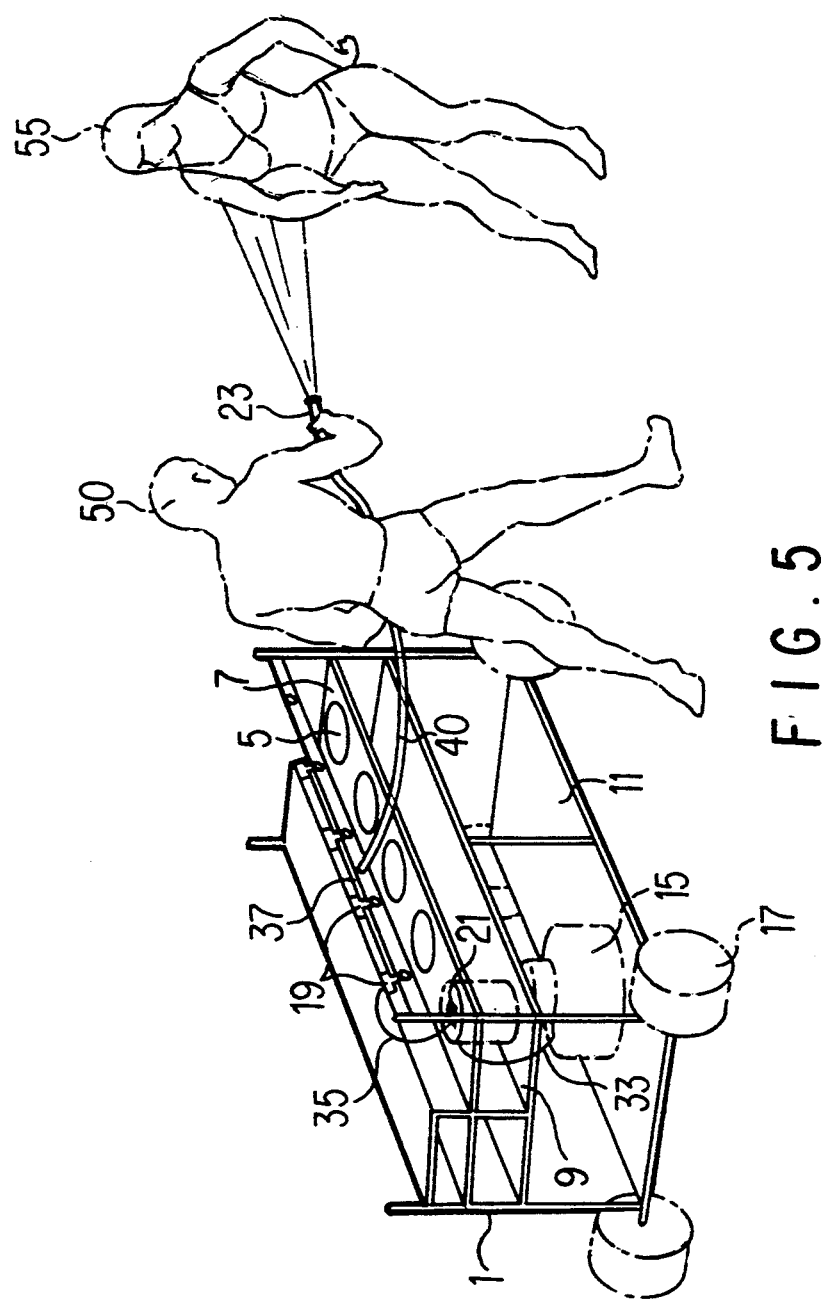
FIG. 5 is an illustration of the apparatus of the present invention during use.

Referring now to the drawings, wherein like reference numerals designate identical or corresponding parts throughout the several views, and more particularly to FIG. 1 thereof, FIG. 1 is a side view of the apparatus of the present invention which is utilized to apply skin protection fluids onto an individual's skin. The apparatus includes a frame 1 for holding a plurality of pressure containers 3. For illustrative purposes, FIGS. 1, 3 and 5 only show a single pressure container, however the number of pressure containers to be mounted on the frame is based on the user's preference. As illustrated in the perspective view of FIG. 3, the pressure containers 3 can be positioned within receiving holes 5 provided on a shelf 7 of the frame 1. A further shelf 9 can be provided to support each of the pressure containers 3 within the receiving holes 5. A bottom shelf 11 can be provided on the frame 1 for supporting an air compressor 15 thereon. To clearly illustrate the mounting of the pressure containers 3 and air compressor 15 on the frame 1, the perspective view of FIG. 3 does not illustrate the fluid interconnection between the elements.

Figure 4:
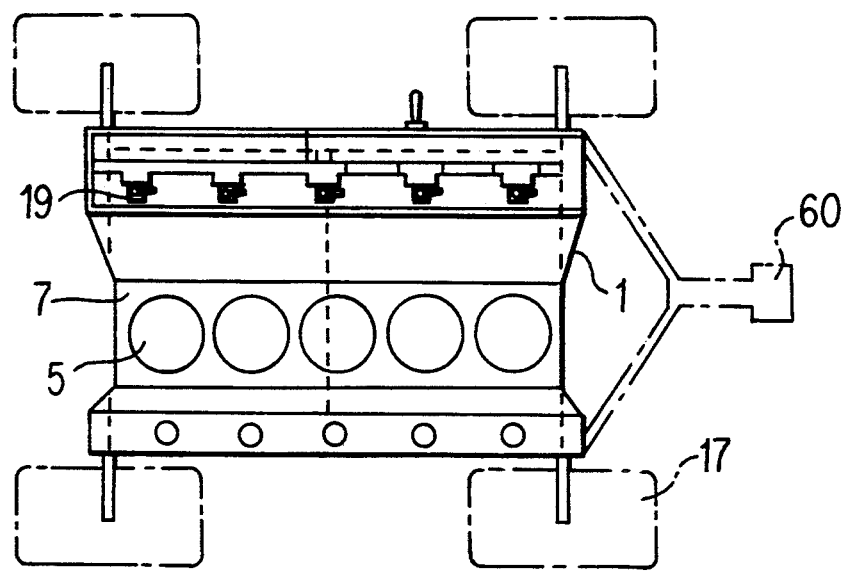
FIG. 4 is a top view of the apparatus illustrated in FIGS. 1 and 3.

In an embodiment of the present invention, the frame 1 can include a handle 60 and can be mounted on all-terrain tires 17 as illustrated in FIG. 4 to permit an individual selling and applying the skin protection fluids to easily transport the frame with the compressor and pressure containers mounted thereon along the sand of a beach.

As noted above, the pressure containers 3 are mounted within the holes 5 on the frame 1. The pressure container can be a known pressure container such as a pressure container model 80-228 manufactured by Binks Manufacturing Company. As illustrated in FIG. 1, the pressure container 3 includes an outlet 3a and an adjustable pressure regulator 21 having a pressure gauge for adjusting the discharge pressure from the air compressor 15.

An open/close valve 19 corresponding to each of the pressure containers can be mounted on a further shelf 39 of the frame 1 or can be supported on the frame 1 through a variety of other known means. A fluid connection pipe, tube or hose 35 for each of the pressure containers 3 connects the outlet 3a of each of the pressure containers 3 to the open/close valve 19. The open/close valve 19 controls the flow of fluid from the pressure container.

The air compressor 15 is mounted on the shelf 11 of the frame 1. The connection between the air compressor 15 and pressure containers 3 can be realized by, for example, a flexible hose, pipe or tube 33 such that the connection can be achieved in a known manner.

Figure 2:
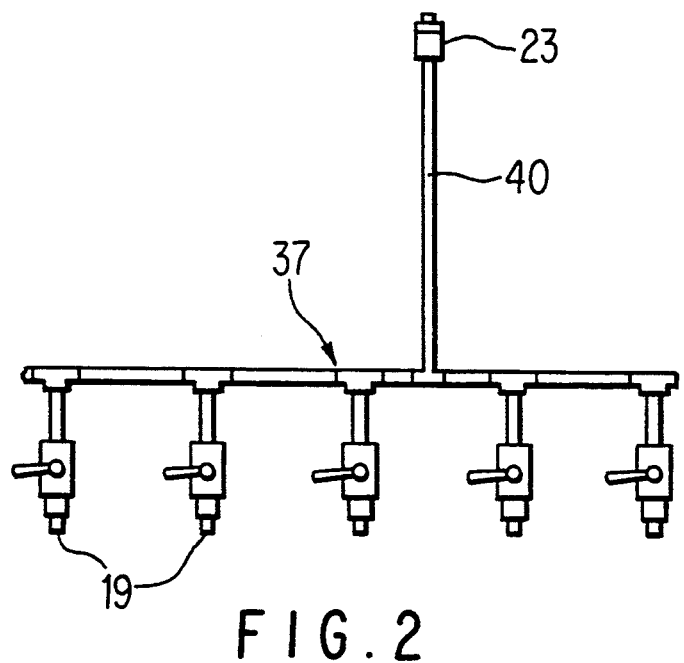
FIG. 2 is an illustration of the control valves and nozzle of the pressure containers.

As illustrated in FIG. 2, each of the open/close valves 19 are connected via a multi-way connection means 37 to a single adjustable control nozzle 23 having an adjustable orifice through the use of a flexible tube or galvanized pipe 40. The length of the galvanized pipe and tubing is a design consideration and basically depends on the user's preference.

The frame 1 may also include a hook 27 (FIG. 1) for permitting the pipe or hose 40 which serves as the connection between the adjustable nozzle 23 and each of the open/close valves 19 to be wrapped thereon for storage.

Each of the pressure containers 3 contain a skin protection fluid having a different skin protection factor. The fluids can be well-known suntan lotions and oils. In the context of the present invention, the applicant has determined that lotions cannot be delivered through a standard siphon feed system. Also, although oils could be delivered with a siphon feed system, the necessary pressure for delivering oil is excessive and may cause an overspray or uncontrolled dispersion of the product.

The apparatus of the present invention provides for the spraying of a desired skin protection fluid with the lowest possible air pressure. Lower air pressure allows maximum efficiencies and reduces overspray to thereby minimize waste.

In the present invention, a plurality of skin protection fluids having different skin protection factors can be selectively applied to an individual by way of a single nozzle 23. Since skin protection lotions and oils having different skin protection factors are creamy in nature and have different fluid properties and viscosities, it is therefore necessary to properly control and adjust air pressure and fluid nozzle orifice size based on the selected skin protection fluid. This facilitates the delivery of the selected skin protection fluid. The following Table I illustrates the range of necessary air pressures and nozzle orifice sizes for delivering skin protection fluid of different skin protection factors.

TABLE I

| PRODUCT | SOURCE AIR PRESSURE | TANK AIR PRESSURE | | NOZZLE ORIFICE SIZE |
|---|---|---|---|---|
| | | min. | max. | |
| Sun lotion SPF 2 | 120 PSI | 45– | 60 PSI* | .110 CM |
| Sun lotion SPF 4 | 120 PSI | 45– | 60 PSI | .110 CM |
| Sun lotion SPF 6 | 120 PSI | 45– | 60 PSI | .110 CM |
| Sun lotion SPF 8 | 100 PSI | 25– | 30 PSI | .086 CM |
| Sun lotion SPF 15 | 100 PSI | 20– | 35 PSI | .086 CM |
| Sun lotion SPF 30 | 100 PSI | 20– | 35 PSI | .086 CM |
| Sun lotion SPF 40 | 100 PSI | 20– | 35 PSI | .086 CM |
| Suntan Oil SPF 2 | 60 PSI | 15– | 35 PSI | .040 CM |
| Screening Lotion | | | | |

TABLE I-continued

| PRODUCT | SOURCE AIR PRESSURE | TANK AIR PRESSURE min. | TANK AIR PRESSURE max. | NOZZLE ORIFICE SIZE |
|---|---|---|---|---|
| SPF 30 | 100 PSI | 20– | 35 PSI | .070 CM |
| SPF 45 | 100 PSI | 20– | 35 PSI | .070 CM |
| Moisturizing Lotion | 120 PSI | 40– | 60 PSI | .110 CM |

*minimum air pressure moves product efficiently
maximum air pressure is that pressure where product continues to efficiently move, exceeding maximum air pressure contributes to excessive overspray and waste of material In the present invention, the rate of airflow measured in cubic feet per minute and the selected skin protection fluid determines orifice size. In determining the correct orifice size, cubic feet per minute at varying air pressure was a factor, since failure to use the correct combination would result in failure to move the product or excessive overspray causing waste of the product.

During use, an individual selects a pressure container 3 containing the desired skin protection fluid that he or she wishes to have applied on his or her skin. As illustrated in FIG. 5, the operator 50 of the apparatus then adjusts the pressure regulator 21 positioned on the selected pressure container 3 and the nozzle orifice size based on the type of skin protection factor selected. As already set forth, the above-noted Table I illustrates the ranges of air pressures and nozzle orifice sizes which are necessary to deliver different kinds of skin protection fluids. As further illustrated in FIG. 5, the user 50 thereafter points the nozzle 23 at the individual 55 to be sprayed and opens the open/close valve 19 of the selected container 3 to thereby provide for an efficient spraying of the skin protection fluid onto the individual's skin. With the apparatus of the present invention, the user can apply skin protection fluid on any part of the individual which he or she wishes to have sprayed.

It is noted that an improper air pressure selection or nozzle orifice size can cause waste of the product and too high of an air pressure may cause an uncomfortable sensation on an individual's skin. If the selected pressure is too low, an efficient application of the skin protection fluid onto the individual's skin could not be achieved. The present invention provides for a range of pressures and orifice sizes based on the fluid properties, viscosity and creamy nature of each of the variety of skin protection fluids to achieve an efficient and proper spraying of the skin protection fluid onto the individual's skin. Additionally, the pressures and orifice sizes of the present invention provide for a spraying which achieves a cooling sensation on the individual's skin. The result is an even application of skin protection fluid on the individual's skin which allows the individual to sunbathe, exercise or swim with full protection from the harmful rays of the sun.

Due to the fact that the frame 1 of the present invention includes containers having skin protection fluids of different SPF factors, the present invention can be used to apply skin protection fluids on numerous individuals who require skin protection fluids having different SPF factors.

By mounting the frame on all-terrain tires 17 as illustrated in FIGS. 1 and 4, a user of the apparatus of the present invention can transport the apparatus along the beach and provide individuals on the beach with their choice of skin protection fluid in an efficient and effective manner. The utilization of the all-terrain tires 17 enables the frame 1 to be very mobile even on soft surfaces such as sand. Additionally, although the illustrated frame 1 is capable of holding five pressure containers, it is recognized that the frame 1 can be designed to hold any specific number of pressure containers.

Accordingly, the present invention provides for an apparatus and method for dispensing a variety of skin protection lotions and oils depending upon an individual's particular needs or preference. The system applies lotions and oils directly to the skin and an operator of the system will be able to spray lotions evenly on the individual. An operator will also be able to easily apply sun protection lotions and oils onto hard-to-reach areas of an individual such as the individual's back. The system can be utilized in a single station or may be made portable and transported along different locations of the beach by utilizing all-terrain tires.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A method for selectively applying a variety of skin protection fluids on an individual's skin, the method comprising the steps of:

storing a plurality of skin protection fluids having a different skin protection factor in a plurality of pressure containers such that each pressure container contains a distinct skin protection fluid, each of said pressure containers comprising an outlet for permitting a discharge of said skin protection fluid;

connecting each of said pressure containers containing said skin protection fluid to an air compressor, the outlet of each of said pressure containers being operatively connected to an adjustable air pressure regulator for controlling a discharge air pressure from said air compressor and a control valve for controlling a flow of said skin protection fluid from the pressure container;

fluidly connecting the flow control valve of each of said pressure containers to a single control nozzle having an adjustable orifice;

selecting a skin protection fluid to be applied to the individual's skin from said plurality of skin protection fluids in each of said pressure containers;

adjusting the air pressure regulator of said pressure container containing said selected skin protection fluid so as to provide a desired discharge air pressure based on at least a viscosity of the selected skin protection fluid for discharging said selected skin protection fluid;

opening the control valve of said pressure container containing said selected skin protection fluid to permit a discharge of said selected skin protection fluid; and applying the selected skin protection fluid on the individual through said nozzle.

2. A method according to claim 1, comprising the further step of:

adjusting a size of the orifice of said nozzle based on said desired discharge air pressure and said selected skin protection fluid so as to control a spraying of said selected skin protection fluid discharged through said nozzle.

3. A method according to claim 2, wherein said orifice size is within a range of 0.040 to 0.110 cm.

4. A method according to claim 1, wherein said desired discharge air pressure is within a range of 15 to 60 psi.

5. A method for selectively spraying a variety of skin protection fluids on an individual's skin, the method comprising the steps of:

selecting a skin protection fluid to be sprayed onto an individual's skin from a variety of skin protection fluids having different skin protection factors and stored in a plurality of pressure containers operatively connected to open/close valves;

adjusting a discharge air pressure on the pressure container containing the selected skin protection fluid based on at least a viscosity of the selected skin protection fluid;

opening the open/close valve of only the pressure container containing the selected skin protection fluid to permit a discharge of the selected skin protection fluid through the open/close valve; and using a nozzle having an adjustable orifice and fluidly connected to all of said open/close valves of the pressure containers to spray the selected skin protection fluid onto the individual's skin.

6. A method according to claim 5, comprising the further step of:

adjusting an orifice size of said nozzle based on the adjusted discharge air pressure and the selected skin protection fluid.

7. An apparatus for applying a variety of skin protection fluids on an individual's skin, the apparatus comprising:

a plurality of pressure containers, each one of said pressure containers containing a skin protection fluid having a different skin protection factor each in the range of 2–45 and an outlet for discharging said skin protection fluid, each of said pressure containers being operatively connected to a control valve for controlling a flow of said skin protection fluid from said pressure container;

an air compressor operatively connected to each of said pressure containers to provide a discharge pressure for discharging said skin protection fluid from the pressure container through said outlet;

a single nozzle for applying the skin protection fluid discharged from said pressure container to an individual's skin, said single nozzle having an adjustable orifice and being fluidly connected to each of said control valves of said pressure containers; and an adjustable pressure regulator operatively connected to each one of said pressure containers for adjusting the discharge pressure from said air compressor based on at least a viscosity of the skin protection fluid selected to be discharged and applied to the individual's skin, wherein a size of said orifice of the nozzle is adjusted based on the selected discharge pressure and the selected skin protection fluid.

8. An apparatus according to claim 7, further comprising a frame for holding said air compressor and each of said pressure containers containing said skin protection fluids.

9. An apparatus according to claim 8, wherein said frame is a mobile frame having all-terrain tires.

10. An apparatus according to claim 7, wherein said discharge pressure is in a range of 15 to 60 psi.

11. An apparatus according to claim 7, wherein a size of said orifice is in a range of 0.040 to 0.110 cm.

* * * * *